United States Patent
Padia et al.

(10) Patent No.: US 7,619,099 B2
(45) Date of Patent: Nov. 17, 2009

(54) REDUCTION OF ACRYLIC ACID IN THE PRODUCTION OF MALEIC ANHYDRIDE

(75) Inventors: Ashok S. Padia, Glen Rock, NJ (US); Arie Bortinger, Ridgewood, NJ (US); Gianluca Mazzoni, Bergamo (IT); Tiziana Monti, Bologna (IT)

(73) Assignees: Scientific Design Company, Inc., Little Ferry, NJ (US); Lonza S.p.A., Bergamo (IT)

( * ) Notice: Subject to any disclaimer, the term of this patent is extended or adjusted under 35 U.S.C. 154(b) by 331 days.

(21) Appl. No.: 11/405,134

(22) Filed: Apr. 17, 2006

(65) Prior Publication Data

US 2007/0244332 A1 Oct. 18, 2007

(51) Int. Cl.
*C07D 307/60* (2006.01)
(52) U.S. Cl. ............................ 549/259; 549/260
(58) Field of Classification Search ............ 549/259, 549/260
See application file for complete search history.

(56) References Cited

U.S. PATENT DOCUMENTS 4,795,818 A * 1/1989 Becker et al. ............... 549/260
5,185,455 A * 2/1993 Ebner ......................... 549/259
5,360,916 A 11/1994 Padia et al. ................. 549/259
5,945,368 A 8/1999 Felthouse et al. ........... 502/209
6,194,587 B1 2/2001 Doshi ......................... 549/258
6,858,561 B2 2/2005 Bortinger et al. ............ 502/209

* cited by examiner

*Primary Examiner*—Bernard Dentz
(74) *Attorney, Agent, or Firm*—Scully, Scott, Murphy & Presser, P.C.

(57) ABSTRACT

An improved process for the production of maleic anhydride by the catalytic oxidation of n-butane. Maleic anhydride is produced by reacting n-butane gas with oxygen gas or an oxygen-containing gas, in the presence of a vanadium phosphorus oxide catalyst. A trialkyl phosphite or trialkyl phosphate component is continuously added to the gases in an amount of from about 0.5 ppm to about 4 ppm by weight of elemental phosphorus in the trialkyl phosphate or trialkyl phosphite component. Heat is applied to the gases at a temperature of from about 400° C. to about 440° C. while maintaining a maximum temperature of gases present in the reaction of about 480° C. A simultaneous conversion of n-butane to maleic anhydride of about 84% or more and a conversion of n-butane to by-product acrylic acid of about 1.5% or less is achieved.

20 Claims, No Drawings

REDUCTION OF ACRYLIC ACID IN THE PRODUCTION OF MALEIC ANHYDRIDE

BACKGROUND OF THE INVENTION

1. Field of the Invention

This invention relates to an improved process for the production of maleic anhydride by the catalytic oxidation of n-butane.

2. Description of the Related Art

It is well known in the art that maleic anhydride may be manufactured by the vapor phase oxidation of n-butane as it flows through a fixed bed reactor containing a vanadium phosphorus oxide (VPO) catalyst. N-butane in admixture with air is brought into contact with a VPO catalyst under conditions such that the n-butane is oxidized to maleic anhydride. The effluent from the reactor may be cooled to partially condense the product maleic anhydride from the effluent gases. The gaseous product, with or without partial maleic anhydride removal, is scrubbed using a solvent, usually water or an organic solvent, to recover the maleic anhydride. The remaining gases, containing unconverted n-butane, are commonly incinerated in an effluent gas incinerator prior to venting to atmosphere. Useful processes, as well as VPO catalysts for the production of maleic anhydride from n-butane are known from U.S. Pat. Nos. 6,194,587; 5,360,916 and 6,858, 561, which are incorporated herein by reference. U.S. Pat. No. 5,360,916 discloses a two stage process for maleic anhydride production wherein n-butane is oxidized in a first reaction zone and the effluent from this zone is passed together with supplemental n-butane to a second reactor in series in order to complete production of the maleic anhydride. In U.S. Pat. No. 5,360,916, butane is oxidized with molecular oxygen in a dilute state by bringing a mixture of vaporized butane and air having a controlled butane content into the presence of a vanadium phosphorus oxide catalyst in a first oxidation zone under controlled pressure and temperature conditions, cooling the gaseous effluent from the first oxidation zone to a temperature in the range of 50° C. to 300° C., introducing a controlled amount of butane into the cooled gaseous effluent from the first oxidation zone, introducing the cooled butane-enriched stream into the second oxidation zone, and bringing the thus butane-enriched mixture into contact with a vanadium-phosphorus-oxygen catalyst disposed in the second zone. U.S. Pat. No. 6,858,561 teaches a process for preparing a catalyst for maleic anhydride production.

During the known processes for the production of maleic anhydride by the catalytic oxidation of n-butane, acrylic acid is formed as a nuisance by-product of the reaction. In maleic anhydride plants, downstream process equipment such as heat exchangers, and distillation equipment are often fouled after prolonged operation with a polyacrylic polymer derived from the accumulation and self-reaction of acrylic acid. Such fouling occurs where the acrylic acid polymerizes and obstructs and reduces the performance of the distillation column. There is therefore a need in the art for an improved process which inhibits the formation of acrylic acid by-product while preserving maleic anhydride yield.

One method for reducing acrylic acid production suggested by U.S. Pat. No. 5,945,368 is to employ a phosphorus vanadium oxide catalyst containing molybdenum. While this technique apparently reduces the amount of acrylic acid produced, the yield of maleic anhydride is also reduced.

In a typical commercial process for the production of maleic anhydride by the catalytic oxidation of n-butane, the rate of n-butane conversion to maleic anhydride is approximately 82 wt. %-83 wt. % which gives a maleic anhydride yield of 97+wt. % and an acrylic acid yield of approximately 1.7 wt. % to 1.8 wt. %. Under the conditions of the present improvement, conversion of n-butane to maleic anhydride is increased to about 84% or more, and acrylic acid yield is reduced, typically to below 1.4 wt %, without decreasing maleic anhydride yield.

SUMMARY OF THE INVENTION

The invention provides a process for the production of maleic anhydride which comprises reacting n-butane gas with oxygen gas or an oxygen-containing gas, in the presence of a vanadium phosphorus oxide catalyst; continuously adding at least one trialkyl phosphite or trialkyl phosphate component to the gases in an amount of from about 0.5 ppm to about 4 ppm by weight of elemental phosphorus in the trialkyl phosphate or trialkyl phosphite component, based on the total amount of the n-butane gas and oxygen gas or an oxygen-containing gas, while applying heat to the gases at a temperature of from about 400° C. to about 440° C. and maintaining a maximum temperature of gases present in the reaction of about 480° C., to simultaneously achieve a conversion of n-butane to maleic anhydride of about 84% or more and a conversion of n-butane to by-product acrylic acid of about 1.5% or less.

The invention also provides a process for the production of maleic anhydride which comprises providing a fixed bed tubular reactor containing a vanadium phosphorus oxide catalyst;

flowing a continuous stream of n-butane gas, and oxygen gas or an oxygen-containing gas into the tubular reactor; contacting the n-butane gas, and oxygen gas or an oxygen-containing gas with the vanadium phosphorus oxide catalyst and causing the n-butane gas, and oxygen gas or an oxygen-containing gas to react in the presence of a vanadium phosphorus oxide catalyst within the fixed bed tubular reactor; continuously adding at least one trialkyl phosphite or trialkyl phosphate component to the gases in an amount of from about 0.5 ppm to about 4 ppm by weight of elemental phosphorus in the trialkyl phosphate or trialkyl phosphite component, based on the total amount of the n-butane gas and oxygen gas or an oxygen-containing gas, while applying heat to the gases at a temperature of from about 400° C. to about 440° C. and maintaining a maximum temperature of gases present in the reaction of about 480° C., to simultaneously achieve a conversion of n-butane to maleic anhydride of about 84% or more and a conversion of n-butane to by-product acrylic acid of about 1.5% or less.

DETAILED DESCRIPTION OF THE INVENTION

The oxidation of the n-butane to maleic anhydride may be accomplished by contacting a stream of gaseous n-butane in low concentrations in a stream of oxygen or oxygen containing gas with the VPO catalyst in a heated, standard tubular oxidation reactor.

Air is a useful source of oxygen, but mixtures of oxygen and diluent gases, such as nitrogen also may be employed. Air enriched with oxygen may also be used. A gaseous feed stream contains oxygen or an oxygen containing gas such that the amount of oxygen usually ranges in an amount of from about 15 vol % to about 30 vol % based on the total volume of n-butane plus oxygen or an oxygen containing gas feed stream, more usually from about 18 vol % to about 25 vol %, and still more usually from about 19 vol % to about 21 vol %. The gaseous feed stream then contains n-butane such that the amount of n-butane usually ranges in an amount of from about 0.5 vol % to about 3.0 vol % based on the total volume of n-butane plus oxygen or oxygen containing gas feed stream, more usually from about 1.0 vol % to about 2.5 vol %, and still more usually from about 1.5 vol % to about 2.2 vol %. Higher concentrations of n-butane may be employed, provided the amount avoids explosive hazards. Lower concentrations of n-butane, i.e. less than about one mole percent, will reduce the total productivity obtained at equivalent flow rates and thus are not normally economically employed. Diluent gases such as nitrogen may also be incorporated into the feed stream in amounts easily determined by those skilled in the art.

Continuously added to the gas feed stream is at least one trialkyl phosphate or trialkyl phosphite component. Useful trialkyl phosphate or trialkyl phosphite components non-exclusively include trimethyl phosphate, triethyl phosphate, tripropyl phosphate, trimethyl phosphite, triethyl phosphite, and tripropyl phosphite, and combinations thereof. Useful amounts of trialkyl phosphate or trialkyl phosphite component added to the gaseous feed stream is an amount of from about 0.5 ppm to about 4 ppm, preferably from about 1 ppm to about 3 ppm by weight of elemental phosphorus in the trialkyl phosphate or trialkyl phosphite based on the total amount of the gases.

A variety of reactors are useful and multiple tube heat exchanger type reactors are satisfactory. The tubes of such reactors may vary in inside diameter from about 0.5 inch (1.27 cm) to about 1.5 inches (3.8 cm), and the length may be varied from about 5 feet (1.524 meters) to about 25 feet (7.62 meters) or more. The oxidation reaction is an exothermic reaction and, therefore, relatively close control of the reaction temperature should be maintained. It is desirable to have the surface of the reactors at a relatively constant temperature and some medium to conduct heat from the reactors is necessary to aid temperature control. Such media may be molten sulfur, mercury, molten lead, and the like, but it has been found that eutectic salt baths are most satisfactory. One such salt bath is a sodium nitrate-sodium nitrite-potassium nitrite eutectic constant temperature mixture. An additional method of temperature control is to use a metal block reactor whereby the metal surrounding the tube acts as a temperature regulating body. As will be recognized by one skilled in the art, the heat exchange medium may be kept at the proper temperature by heat exchangers and the like. The reactor or reaction tubes may be iron, stainless steel, carbon steel, nickel, glass tubes such as Vycor and the like which have excellent long life under the conditions for the reactions described herein. Normally, the reactors contain a preheat zone of an inert material such as ¼' Alundum pellets, inert ceramic balls, nickel balls or chips and the like, present at about ½ to ¹⁄₄₀ the volume of the active catalyst present. The reactors may comprise a single stage, dual sequential stages or multiple sequential stages as described in U.S. Pat. No. 6,194,587. The reactor may be provided with one or more salt circuits along the reactor tubes. Ordinarily, an entire reactor has a single salt circuit maintained at the operating temperature, but it may be desired to have a first temperature zone extending from the inlet of the reactor to any desired downstream point and a second temperature zone extending from that point to the outlet of the reactor.

The catalyst which is suitably used in forming the catalyst beds inside the reactor for carrying out the oxidations can be any of the vanadium phosphorus oxide contact catalysts used in the butane oxidation art and the invention is in no way limited to any particular catalyst.

Broadly, the vanadium phosphorus oxide catalysts comprise vanadium, phosphorus and oxygen combined as a complex. The overall ratio of vanadium to phosphorus in the catalyst will have an atomic ratio of about 1/2 to 3 atoms of phosphorus per atom of vanadium. The vanadium phosphorus oxygen catalyst may also contain various stabilizers and metal additives generally in percents of less than 15 weight percent based on the total weight of vanadium and phosphorus. The atomic ratio of oxygen to the remaining components of the catalyst, when the catalyst is in the process of being used to catalyze the oxidation, is difficult to determine and is probably not constant due to the competing reactions of oxidation and reduction taking place during the reaction at high temperatures. The overall ratio of oxygen to the combined atoms of vanadium and phosphorus at room temperature would be such as about 2 to 6 atoms of oxygen per the combined atoms of vanadium and phosphorus. The catalyst is present during the reaction as an oxide of vanadium and phosphorus. The catalytic material from which the catalyst structure is made is a vanadium-phosphorus-oxygen complex type catalyst for the conversion of hydrocarbons to the corresponding anhydride. The catalyst usually contains at least one modifying component, Me, which is a metal, including the rare earth metals, an alkali metal, an alkaline earth metal, or mixture thereof.

The precise structure of the present complex catalyst has not been determined; however, a preferred complex may be represented by formula $VP_aMe_bO_x$ wherein Me is the modifying component, a is from about 0.90 to about 1.3, b is from about 0.001 or greater, preferably from about 0.005 to about 0.4. The representation is not an empirical formula and has no significance other than representing the atom ratio of the active metal components of the catalyst. The x has no determinate value and can vary widely, depending on the combinations within the complex, and is selected to complete the valence requirements of the complex. Oxygen present and $O_x$ is representative of this. Among the various Me components used either alone or in combination with each other are elements which are metal and metaloids from Group Ia, Ib, IIa, IIb, IIIa, IIIb, IVa, IVb, Va, the 4th period of VIIIb, and the rare earths of the Periodic Table of elements. Some specific Me components may be Cu, Ag, Zn, Cd, Al, Ga, In, Sc, Y, La, Ge, Sn, Pb, Ti, Zr, Sb, Bi, As, Fe, Co, Ni, Ce, Pr, Nd, Cr, Li, Na, K, Rb, Fr, Nb, Te, W, Pd, Mn, Mo, Re, Sm, Hf, Ta, Th, U, Sn, B, Si, Mg, Ba, Tb and Eu. More preferred Me components are Cu, Mo, Ni, Co, Cr, Nd, Ce, Ba, Y, Sm, Te, Zr, W, Pd, Ag, Mn, Zn, Re, La, Hf, Ta, Th, U, Eu, Nb, Ru, Li, Mg, B and Si. The Me components may be considered as stabilizers, promoters, modifiers or the like, however, regardless of the characterization the Me components are a part of the catalyst, in that they affect the performance in the oxidation of the n-butane. The activity of the catalyst may be moderated by dispersing 5 to 50% (by volume) discrete inert structures, such as alumina. Particularly advantageous catalysts are those described in U.S. Pat. Nos. 4,251,390; 3,980,585 and 4,105, 586. The catalyst may be employed as pellets, disc, flakes, wafers, or any other convenient shape which will facilitate its use in the tubular reactors employed for this type of vapor phase reaction. For example the catalyst may be prepared as tablets having a hole or bore therethrough as disclosed in U.S. Pat. No. 4,283,307. Generally, an unsupported catalyst will have higher surface area than supported catalysts. The final catalyst particle size for this arrangement is usually about 2½ to about 10 Tyler mesh. After activation the surface area is preferably less than 100 $m^2/g$ and preferably at least 1 $m^2/g$ and more preferably at least 5 $m^2/g$.

The flow rate of the gaseous feed stream through the reactor may be varied within rather wide limits but a useful range of operations is at a gas hourly space velocity (GHSV) of from about 1,000 to about 4,000, preferably from about 1,500 to about 3,000, and more preferably from about 1,800 to about 2,800. Residence times of the gas stream in contact with the catalysts will normally be less than about 4 seconds, more preferably less than about one second, and down to a rate where less efficient operations are obtained. The gaseous feed stream is usually supplied to the reactors at an inlet pressure of from about 0.6 kg/cm$^2$ gauge to about 4.0 kg/cm$^2$ gauge, preferably from about 1.0 kg/cm$^2$ gauge to about 3.0 kg/cm$^2$ gauge, and more preferably from about 1.2 kg/cm$^2$ gauge to about 2.5 kg/cm$^2$ gauge.

The temperature of reaction may be varied, but normally the reaction should be conducted at temperatures within a rather narrow range. The temperature in the reactor will also depend to some extent upon the size of the reactor and the n-butane concentration. The oxidation reaction is exothermic and once reaction is underway, the main purpose of the salt bath or other media is to conduct heat away from the walls of the reactor and control the reaction. The reactors are heated to an outside temperature of from about 380° C. to about 460° C., preferable from about 390° C. to about 450° C., and more preferably from about 400° C. to about 430° C. Under useful operating conditions, the maximum temperature of the gas in the reactor, measured by a thermocouple or other probe, is about 430° C. to about 470° C. This maximum temperature of the gas along the length of the reactor inside the reactor tube is called "hot spot" and generally needs to be controlled to maintain the stability of reaction. It is known to those skilled in the art that since heat is applied to the outside surface of the reactor tubes, and the reaction itself is exothermic, the temperature profile of the gases present in the reaction is not constant across the diameter of the reaction tubes. Since the oxidation reaction is exothermic, once reaction is underway, a main purpose of the salt bath or other media is to conduct heat away from the walls of the reactor and control the reaction. The flow of salt in the circuit is maintained at a rate such that the above-specified temperature values are achieved. The "hot spot" as defined above is generally 30° C. to 60° C. higher than the temperature of the coolant (generally molten eutectic salt). The higher "hot spot" promotes further oxidation of the maleic anhydride product resulting in reduced yield and also causes the deactivation of the catalyst. However, an important feature of this invention is that the "hotspot" temperature of gases present in the reaction be maintained at a maximum of about 480° C. or less, preferably about 470° C. or less to minimize the loss of yield and possible deactivation of the catalyst. The added phosphorus component aids in suppressing the hotspot temperature.

The reaction may be conducted at atmospheric or above atmospheric pressure. The exit pressure will be at least slightly higher than the ambient pressure to insure a positive flow from the reactor. The pressure of the gases must be sufficiently high to overcome the pressure drop through the reactor.

After the effluent gas exists the reactor it is cooled to a range of from about 50° C. to about 200° C. range. The exit gas from the reactor after cooling is usually scrubbed in a water bath to remove maleic anhydride as maleic acid or by an organic solvent to remove maleic anhydride as a solute in the organic solvent. The maleic anhydride may be recovered in a number of ways well known to those skilled in the art. For example, the recovery may be by direct condensation or by absorption in suitable media, with subsequent separation and purification of the maleic anhydride.

According to the invention, a conversion of n-butane to maleic anhydride of about 84% or more is achieved. This more usually in the range of from about 84% to about 94%, and still more usually from about 85% to about 92%. At the same time, the conversion of n-butane to by-product acrylic acid is held to about 1.5% or less, usually from about 1.3% to about 1.0%.

The following non-limiting examples serve to illustrate the invention.

EXAMPLE 1

A catalyst was prepared according to U.S. Pat. No. 6,858, 561. The performance test was done in a 3.6 meter stainless steel reactor tube, 21 mm internal diameter packed with a 3.2 meter catalyst bed height. A thermowell with a length of 3.6 meter and diameter of 4.0 mm was placed in the center of the reactor tube. Butane at a controlled concentration in air is used as feed for catalyst evaluation. The butane concentration was about 1.7% and the air contained about 1.8% moisture. To control the hot spot during the test a moderator such as TMP was used in a concentration of about 1.3 ppm. During the test the conversion was increased and the product distribution was determined. This includes the analysis for acrylic acid and acetic. The test results are summarized in Table 1. The results clearly demonstrate a reduction in the amount of acrylic acid with increase the in conversion. Best operation are to operate at conversion between 84 to 94% in order to obtain both reduction in acrylic acid and while maintaining or even increasing maleic anhydride yield.

TABLE 1

| | EXAMPLE | | | | |
| --- | --- | --- | --- | --- | --- |
| | 1 | 2 | 3 | 4 | 5 |
| % CONVERSION | 77 | 81 | 85.4 | 88.6 | 93.9 |
| Wt. % YIELD | 94 | 97 | 99.2 | 99.4 | 99.3 |
| ACRYLIC ACID, % | 1.89 | 1.77 | 1.41 | 1.24 | 1.07 |
| ACETIC ACID, % | 1.70 | 1.50 | 1.55 | 1.38 | 1.24 |
| % REDUCTION IN ACRYLIC ACID [1] | 0 | 6.3 | 25.4 | 34.4 | 43.4 |

[1] Reduction relative to Example 1

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A process for the production of maleic anhydride which comprises reacting n-butane gas with oxygen gas or an oxygen-containing gas, in the presence of a vanadium phosphorus oxide catalyst; continuously adding at least one trialkyl phosphite or trialkyl phosphate component to the gases in an amount of from about 0.5 ppm to about 4 ppm by weight of elemental phosphorus in the trialkyl phosphate or trialkyl phosphite component, based on the total amount of the n-butane gas and oxygen gas or an oxygen-containing gas, while applying heat to the gases at a temperature of from about 400° C. to about 440° C. and maintaining a maximum temperature of gases present in the reaction of about 480° C., to simultaneously achieve a conversion of n-butane to maleic anhydride of about 84% or more and a conversion of n-butane to by-product acrylic acid of about 1.5% or less.

2. The process of claim 1 wherein the oxygen-containing gas comprises air.

3. The process of claim 1 wherein the reacting is conducted in a fixed bed tubular reactor.

4. The process of claim 1 wherein the trialkyl phosphate or trialkyl phosphite component comprises at least one of trimethyl phosphate, triethyl phosphate, tripropyl phosphate, trimethyl phosphite, triethyl phosphite, and tripropyl phosphite.

5. The process of claim 1 wherein the oxygen or an oxygen containing gas is present in the reaction such that the amount of oxygen ranges from about 15 vol % to about 30 vol % based on the total volume of the n-butane gas and oxygen gas or an oxygen-containing gas.

6. The process of claim 1 wherein the n-butane gas is present in the reaction in an amount of from about 0.5 vol % to about 3.0 vol % based on the total volume of the n-butane gas and oxygen gas or an oxygen-containing gas.

7. The process of claim 1 wherein the n-butane gas is present in the reaction in an amount of from about 1.0 vol % to about 2.5 vol % based on the total volume of the n-butane gas and oxygen gas or an oxygen-containing gas.

8. The process of claim 1 wherein the n-butane gas is present in the reaction in an amount of from about 1.5 vol % to about 2.2 vol % based on the total volume of the n-butane gas and oxygen gas or an oxygen-containing gas.

9. The process of claim 1 further comprises a diluent gas in combination with the n-butane gas and oxygen gas or an oxygen-containing gas.

10. The process of claim 9 wherein the diluent gas comprises nitrogen.

11. The process of claim 1 wherein the reaction is conducted in a fixed bed tubular reactor.

12. The process of claim 1 wherein the vanadium phosphorus oxide catalyst has the $VP_aMe_bO_x$ wherein Me is the modifying component, a is from about 0.90 to about 1.3, b is from about 0.001 or greater, x is selected to complete the valence of the catalyst; and Me is an element selected from Group Ia, Ib, Ia, IIb, IIIa, IIIb, IVa, IVb, Va, the 4th period of VIIIb, and the rare earths of the Periodic Table of elements.

13. The process of claim 1 wherein the gases flow through the reactor at a gas hourly space velocity of from about 1,500 to about 3,000.

14. The process of claim 1 wherein the gases have a reaction residence time of about 4 seconds or less.

15. The process of claim 1 wherein the gases have an inflow pressure of from about 0.6 $kg/cm^2$ gauge to about 4.0 $kg/cm^2$ gauge.

16. The process of claim 1 wherein maleic anhydride is subsequently recovered.

17. The process of claim 1 wherein the conversion of n-butane to maleic anhydride is from about 84% to about 94%.

18. The process of claim 1 wherein the conversion of n-butane by-product acrylic acid is from about 1.3% to about 1.0%.

19. A process for the production of maleic anhydride which comprises providing a fixed bed tubular reactor containing a vanadium phosphorus oxide catalyst; flowing a continuous stream of n-butane gas, and oxygen gas or an oxygen-containing gas into the tubular reactor; contacting the n-butane gas, and oxygen gas or an oxygen-containing gas with the vanadium phosphorus oxide catalyst and causing the n-butane gas, and oxygen gas or an oxygen-containing gas to react in the presence of a vanadium phosphorus oxide catalyst within the fixed bed tubular reactor; continuously adding at least one trialkyl phosphite or trialkyl phosphate component to the gases in an amount of from about 0.5 ppm to about 4 ppm by weight of elemental phosphorus in the trialkyl phosphate or trialkyl phosphite component, based on the total amount of the n-butane gas and oxygen gas or an oxygen-containing gas, while applying heat to the gases at a temperature of from about 400° C. to about 440° C. and maintaining a maximum temperature of gases present in the reaction of about 480° C., to simultaneously achieve a conversion of n-butane to maleic anhydride of about 84% or more and a conversion of n-butane to by-product acrylic acid of about 1.5% or less.

20. The process of claim 19 subsequently comprising recovering maleic anhydride.

* * * * *